Figure 1:
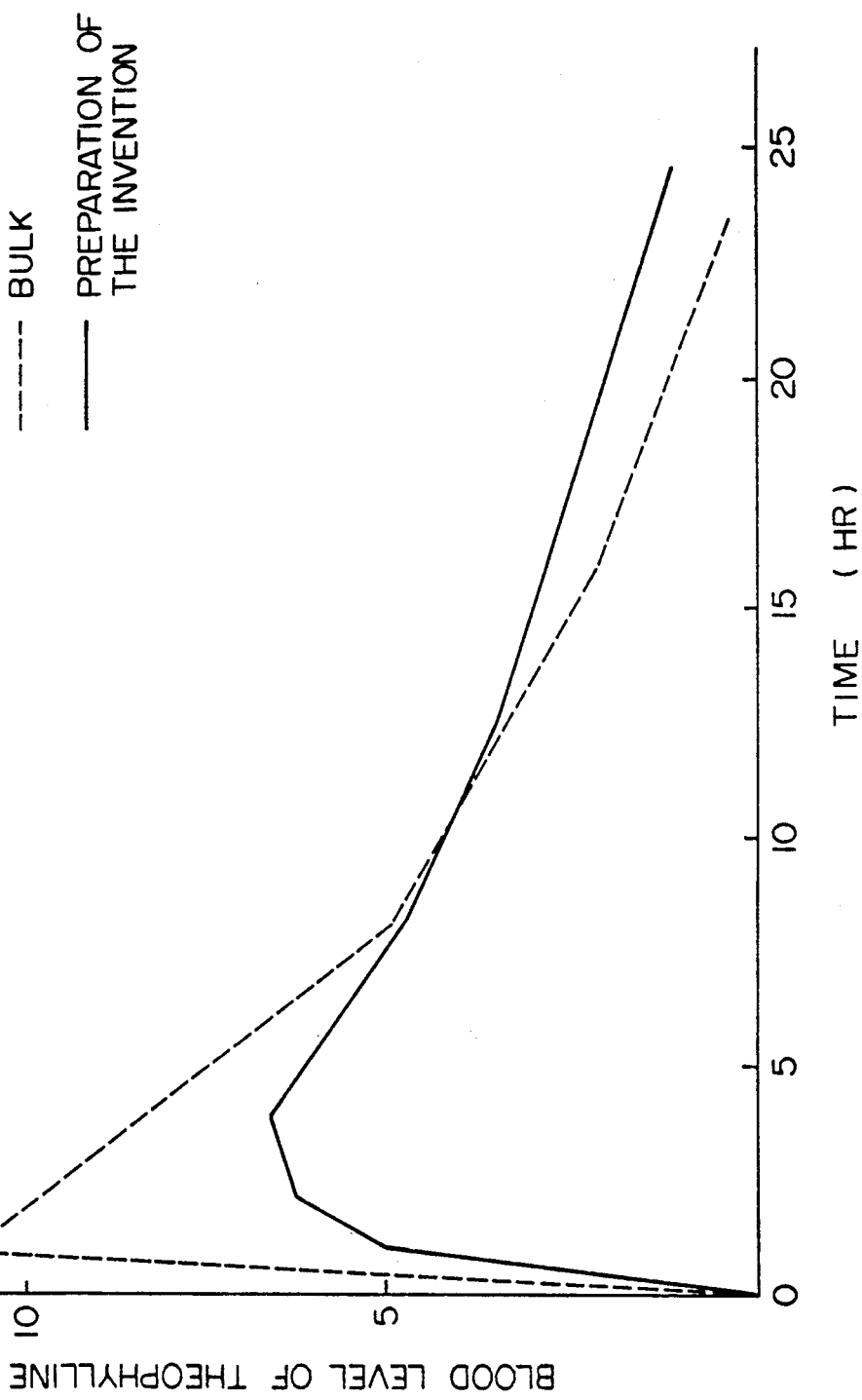

United States Patent [19]

Ozawa et al.

[11] Patent Number: 5,017,383
[45] Date of Patent: May 21, 1991

[54] METHOD OF PRODUCING FINE COATED PHARMACEUTICAL PREPARATION

[75] Inventors: Yasuo Ozawa, Ageo; Ikuo Koyama, Hasuda; Kimihide Shimano, Ageo, all of Japan

[73] Assignee: Taisho Pharmaceutical Co., Ltd., Japan

[21] Appl. No.: 395,594

[22] Filed: Aug. 18, 1989

[51] Int. Cl.$^5$ ............................................. A61K 9/16
[52] U.S. Cl. ..................................... 424/490; 424/489; 424/494; 424/499; 424/475; 424/497; 424/493; 427/212; 427/213.35; 427/213.36; 427/3; 427/213; 426/384; 426/385
[58] Field of Search ............... 427/212, 213.35, 213.36, 427/3, 213; 426/384, 385; 424/489, 494, 490

[56] References Cited

U.S. PATENT DOCUMENTS

| | | | |
|---|---|---|---|
| 3,202,533 | 8/1965 | Sachsel et al. | 427/213 |
| 3,202,731 | 4/1961 | Grevenstuk et al. | 427/213 |
| 4,323,478 | 4/1982 | Adams et al. | 424/499 |
| 4,353,709 | 10/1982 | Nioh et al. | 427/213 |
| 4,576,826 | 3/1986 | Liu et al. | 426/385 |
| 4,753,803 | 6/1988 | Klug et al. | 427/3 |
| 4,816,264 | 3/1989 | Phillips et al. | 427/3 |

FOREIGN PATENT DOCUMENTS

WO88/10150 12/1988 PCT Int'l Appl. .

Primary Examiner—Thurman K. Page
Assistant Examiner—James M. Spear
Attorney, Agent, or Firm—Lorusso & Loud

[57] ABSTRACT

A method of producing a fine coated pharmaceutical preparation, which includes cooling fine liquid droplets composed of a liquid medium, a drug dissolved or suspended in the liquid medium, and as required, a binder to a temperature of not higher than the freezing point of the liquid medium to form frozen particles of the drug and as required the binder, adjusting the particle sizes of the fine frozen particles, mixing the fine frozen particles with a fine powder of a coating material having a particle diameter smaller than the particles at a temperature higher than the freezing point of the liquid medium to cause the fine powder of the coating material to adhere to the surfaces of the particles, and then removing the liquid medium from the resulting coated particles.

14 Claims, 3 Drawing Sheets

METHOD OF PRODUCING FINE COATED PHARMACEUTICAL PREPARATION

This invention relates to a method of producing a fine coated pharmaceutical preparation, and more specifically, to a fine coated pharmaceutical preparation having a constant drug content and a uniform particle size in a high yield.

For the production of fine coated pharmaceutical preparations, a coacervation method, a method of curing in a liquid, a spray-dry method, and a powder bed method, for example, are known. However, since coated pharmaceutical preparations obtained by these known methods have a broad particle size distribution, it is difficult to take out or dry the coated pharmaceutical preparations. Furthermore, because the drug remains in the solvent, the drug content may differ from particle to particle, or there is a difference in dissolution behavior.

With this background, the present inventors thought that in order to obtain a fine coated pharmaceutical preparation of uniform quality, it would be necessary to separate a uniform pharmaceutical preparation physically from a pharmaceutical preparation having a broad particle size distribution.

But according to the coacervation method, the curing method in a liquid and the spray drying method, the recovery of the preparation excluded by classification requires the introduction of a step of adjusting the concentration of the excluded preparation. Accordingly, these methods have the defect that the equipment becomes large in size, a large amount of solvent is necessary, and therefore, the cost of production becomes high.

The powder bed method is a technique of forming a pharmaceutical preparation involving allowing liquid droplets to fall onto a powder bed. However, since the liquid droplets have a large particle size distribution, it is difficult to obtain a pharmaceutical preparation comprising uniform particles. The present inventors thought that if it is possible to provide a uniform particle size of core particles before coating and to easily recover the preparation separated by classification, it would be possible to produce a uniform fine coated pharmaceutical preparation with good efficiency.

It has now been found in accordance with this invention that when liquid droplets in the powder bed method are frozen, the resulting fine frozen particles are easy to classify, and by mixing the fine frozen particles having a uniform and small particle size obtained by classification with a fine powder of a coating material, the frozen solvent in the particles gradually thaws, and the fine powder of the coating material adheres to the solvent to give a homogeneous fine coated pharmaceutical preparation; and that the preparation excluded by classification can be recovered without changing its composition simply by melting it.

Thus, according to this invention, there is provided a method of producing a fine coated pharmaceutical preparation, which comprises cooling fine liquid droplets composed of a liquid medium, a drug dissolved or suspended in the liquid medium, and as required, a binder to a temperature of not higher than the freezing point of the liquid medium to form frozen particles of the drug and optionally the binder, adjusting the particle sizes of the fine frozen particles, mixing the fine frozen particles with a fine powder of a coating material having a particle diameter smaller than said particles at a temperature higher than the freezing point of the liquid medium to cause the fine powder of the coating material to adhere to the surface of said particles, and then removing the liquid medium from the resulting coated particles.

The method of this invention will be described in further detail.

According to the method of this invention, fine liquid droplets containing a drug are first prepared. The fine liquid droplets may be produced by dissolving or suspending the drug and optionally a binder in the liquid medium.

The drug which is to become the pharmaceutical component of the coated pharmaceutical preparation of this invention may be any drug, but preferably any of those to which a value such as stabilization, slow releasing and bitterness masking can be imparted by formation into a coated pharmaceutical preparation. Specific examples of the drug include antibiotics such as cephalosporin and macrolide; antiflammatory and analgesic agents such as ketoprofen and ketophenylbutazone; antihistamic agents such as promethazine hydrochloride; antitussive agents such as clobutinol hydrochloride and oxeladin tannic acid; antidiarrheic agents such as berberine chloride; antispasmodic agents such as propantheline bromide and papaverine hydrochloride; platelet aggregation inhibiting agents such as ticlopidine hydrochloride; antirheumatic agents such as mefenamic acid and flufenamic acid; cardiotonic agents such as digitoxin and aminophylline; tranquilizers such as chloropromazine hydrochloride and promethazine hydrochloride; gallstone dissolvers such as chenodeoxychloic acid; labor inducer and promotor agents such as dinoprost; and other drugs such as iminoppramine hydrochloride, moperone hydrochloride, fenoprofen calcium and theophylline.

The binder which may optionally be used with these drugs is a material which is soluble or suspendable, preferably soluble, in the liquid medium, and imparts a suitable binding force between the drug particles, between the drug and an additive, and among the drug, additive and coating material. Specific examples of the binder include polyvinyl derivatives such as polyvinylacetaldiethylaminoacetate and polyvinylpyrrolidone; cellulose derivatives such as methylcellulose, ethylcellulose, hydroxypropylcellulose, hydroxypropylmethylcellulose and carboxymethylcellulose or its sodium salt; acrylic polymers such as methacrylic acid/methylmethacrylate copolymer; starch and its derivatives such as starch and dextrin; natural polymeric substances such as gelatin; higher fatty acid esters such as hardened castor oil; and inorganic materials such as talc. Among them, polyvinylacetaldiethylaminoacetate, polyvinylpyrrolidone, hydroxypropylcellulose, hydroxypropylmethylcellulose, carboxymethylcellulose sodium, ethylcellulose, starch and gelatin are suitable.

The proportion of the binder used is not critical. Generally, it is convenient to use 1 to 30 parts by weight, preferably 2 to 15 parts by weight, of the binder per 100 parts by weight of the drug.

The liquid medium used to dissolve or suspend the drug and optionally the binder is not strictly limited, and can be suitably selected depending upon the types of the drug and other components. Examples include water; hydrophilic solvents, for example, monohydric alcohols such as methanol or ethanol and polyhydric alcohols such as glycerol or polyethylene glycol, and ketones such as acetone; and oleophilic solvents, for example, hydrocarbons such as hexane, benzene or toluene, esters such as ethyl acetate or butyl acetate, and halogenated hydrocarbons such as chloroform or methylene chloride. They may be used either singly or in combination with each other. Preferred among them are water, methanol, ethanol, acetone, and mixtures of these.

The total concentration of the drug and the binder as an optional component may be adjusted generally to 5 to 70% by weight, preferably to 7 to 50% by weight, more preferably to 10 to 40% by weight.

As required, other pharmaceutical additives may be added to the solution or suspension of the drug and the binder in the liquid medium. Examples of such additives include solubilizers such as sucrose fatty acid esters; suspending agents such as hydroxypropylcellulose; dispersants such as carboxymethylcellulose; antiseptics such as sorbitan fatty acid esters; corrigents such as saccharin sodium; emulsifiers such as glycerol fatty acid esters; stabilizers such as aluminum monostearate. These additives may be incorporated in amounts which are normally used in pharmaceutical preparations.

The drug, the binder and the additives are added to the liquid medium, and they are uniformly mixed in a suitable stirring device to prepare a solution or suspension.

The resulting solution or suspension is converted into fine liquid droplets after, as required, it is pre-cooled to a temperature slightly higher than the freezing point of the liquid medium.

Conversion into the fine liquid droplets may be effected by an ordinary spraying method, and the use of an atomizer is convenient.

Fine frozen particles containing the drug and optionally the binder and/or the additives are formed by cooling the resulting fine liquid droplets to a temperature not higher than the freezing point of the liquid medium constituting the liquid droplets, preferably to a temperature at least 10° C. lower than the freezing point of the liquid medium, preferably at least 20° C. lower than it.

The freezing point of the liquid medium suitably used in this invention is 0° C. for water, −98° C. for methanol, −116° C. for ethanol, and −95° C. for acetone. The temperature for cooling the fine liquid droplets may be prescribed by using these temperatures as an index.

The cooling may be carried out by spraying the fine liquid droplets into a cooling vessel kept at the above cooling temperature. For example, this can be effected by contacting the fine liquid droplets with liquid nitrogen, liquefied carbon dioxide gas (dry ice) or liquid helium, or by cooling them in an electrically cooled vessel. The most simple and convenient method in practice is to spray the solution or suspension into liquid nitrogen, or spraying the solution or suspension with liquid nitrogen by using two fluid nozzles, whereby the fine liquid droplets are contacted with liquid nitrogen (−196° C.) and frozen.

The fine frozen particles so frozen are then subjected to particle size adjustment (or classification) at a low temperature at which the particles do not substantially thaw to obtain fine frozen particles having a uniform particle diameter. The size adjustment (or classification) may be carried out by using an air classifier, a sieving classifier, etc. according to the desired particle diameter. Generally, a sieving classifier is preferably used.

The size-adjusted (classified) fine frozen particles may have an average particle size of generally 5 to 500 microns, preferably 50 to 300 microns, more preferably 70 to 200 microns.

On the other hand, the particles excluded by size adjustment may be recovered and recycled to the solution or suspension.

The size-adjusted (classified) fine frozen particles of a uniform particle diameter are mixed with a fine powder of a coating material having a smaller particle diameter than the fine frozen particles at a temperature higher than the freezing point of the liquid medium contained in the powder of the coating material to cause the surface of the particles.

Mixing of the fine frozen particles with the fine powder of the coating material is usually carried out by fluidizing the fine powder of the coating material in a mixer of the mechanical stirring type, the air stirring type or the power stirring type, and the fine frozen particles are added to the fluidized fine powder of the coating material at a temperature at which the fine frozen particles are not substantially melted to allow the fine powder to adhere physically to the frozen particles. Then, the mixture is gradually heated to melt the liquid medium in the fine frozen particles gradually. Consequently, the fine powder of the coating material adhering to the fine frozen particles is dissolved to form a coating.

The rate of temperature elevation after the contacting of the fine frozen particles with the fine powder of the coating material may be generally 0.5° to 20° C./min., preferably 2° to 10° C./min., depending upon the solubility of the fine powder of the coating material in the liquid medium.

The particle diameter of the fine powder of the coating material may be varied according to the average particle diameter of the fine frozen particles to be coated. Generally, the suitable particle diameter of the fine coating powder is not more than 1/5, preferably not more than 1/10, of the average particle diameter of the fine frozen particles (after size adjustment).

Examples of the coating material that can be used in this invention include polyvinyl derivatives such as polyvinylacetaldiethylaminoacetate and polyvinylpyrrolidone; cellulose and its derivatives such as methylcellulose, ethylcellulose, hydroxypropylcellulose, hydroxypropylmethylcellulose and hydroxypropylmethylcellulosephthalate; acrylic polymers such as methacrylic acid/methyl methacrylate copolymer (such as "Eudragit ®" of Rörm Pharma Co.); starch and its derivatives such as dextrin; waxes such as beeswax and carnauba wax; higher alcohols such as stearyl alcohol and myristyl alcohol; natural polymeric substances such as gum arabic, agar, tragacanth and gelatin; hydrocarbons such as paraffin; higher fatty acid esters such as hardened castor oil; saccharides such as glucose, fructose and sucrose; and inorganic substances such as talc. As required, they may be used singly or in combination with each other. Suitable among these coating materials are polyvinylacetaldiethylaminoacetate, ethylcellulose, hydroxypropylcellulose, hydroxypropylmethylcellulose, hydroxypropylmethylcellulose phthalate, methylcellulose, acrylic polymers (Eudragit ®), stearyl alcohol, gelatin, carnauba wax, hardened castor oil, sucrose and talc.

The fine particles to which the fine powder of the coating material has adhered are separated from the excess of the fine powder of the coating material by such means as a sieving device or a classifier.

Then, the liquid medium is removed from the coated particles by various known methods, for example, by drying on a fluidized bed. The drying of the coated particles may, if desired, be performed before the classification.

The fine coated pharmaceutical preparation so prepared may be used directly as a fine particulate agent or a granular agent. It may also be administered as a solid preparation by filling it in a capsule, or formulating it into tablets by tableting. Depending upon the type of the drug contained, and particularly for easy administration to infants it may be formulated into a syrup or an oral suspension.

According to the method of this invention, particles having a particle diameter of not more than 50 μm can be coated, and a uniform coated pharmaceutical preparation with a uniform particle size can be obtained in a high yield. This is an advance over the prior art because the coating of particles of this size has previously been considered to be difficult.

The fine coated pharmaceutical preparation produced by the method of this invention contributes to drug stabilization, slow releasing and masking of bitterness.

Further, since this pharmaceutical preparation has improved wetting, flowability and tabletability, its formulating operations are very easy.

The following Examples and Test Examples illustrate the present invention more specifically.

Figure 2:
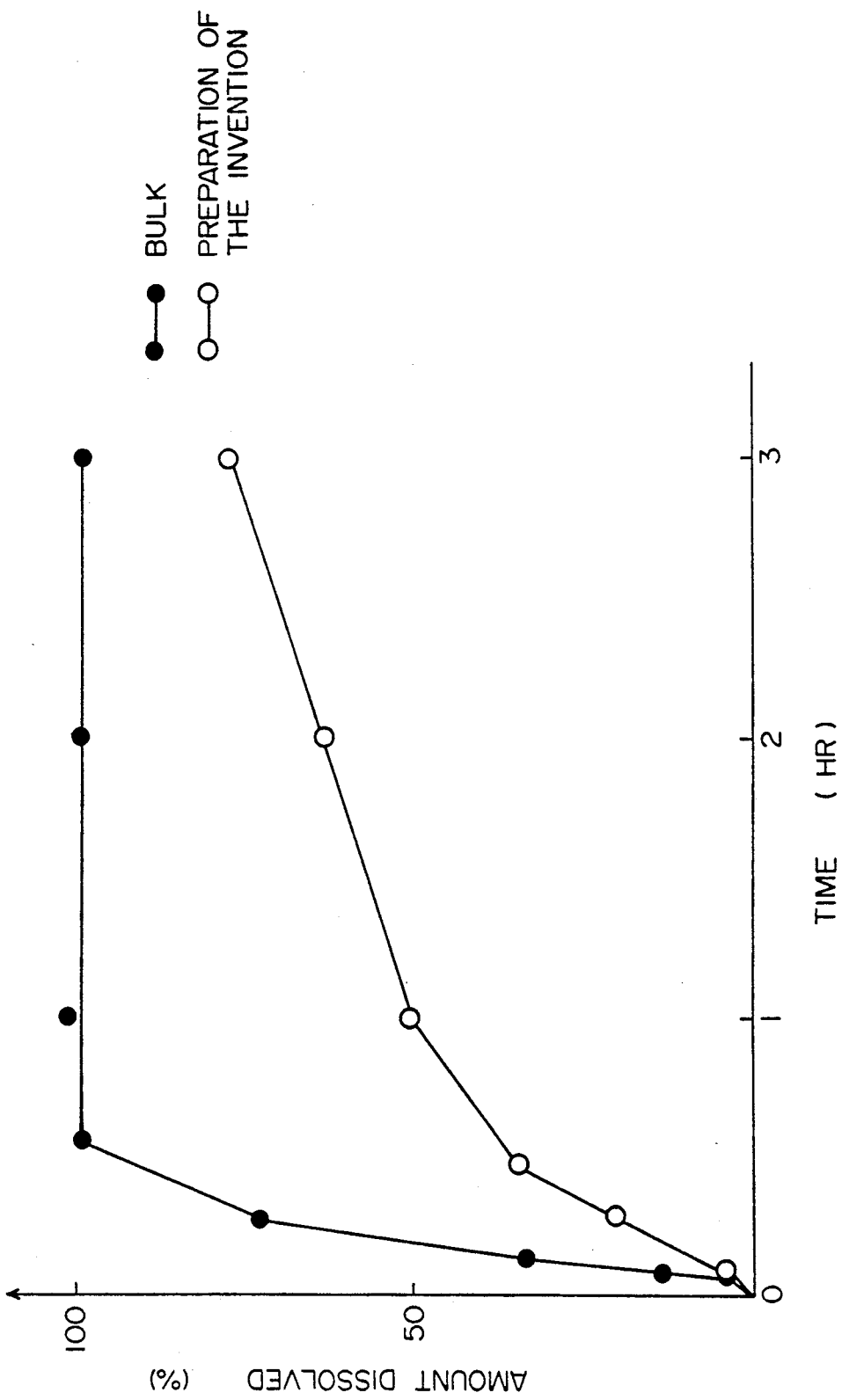
Figure 3:
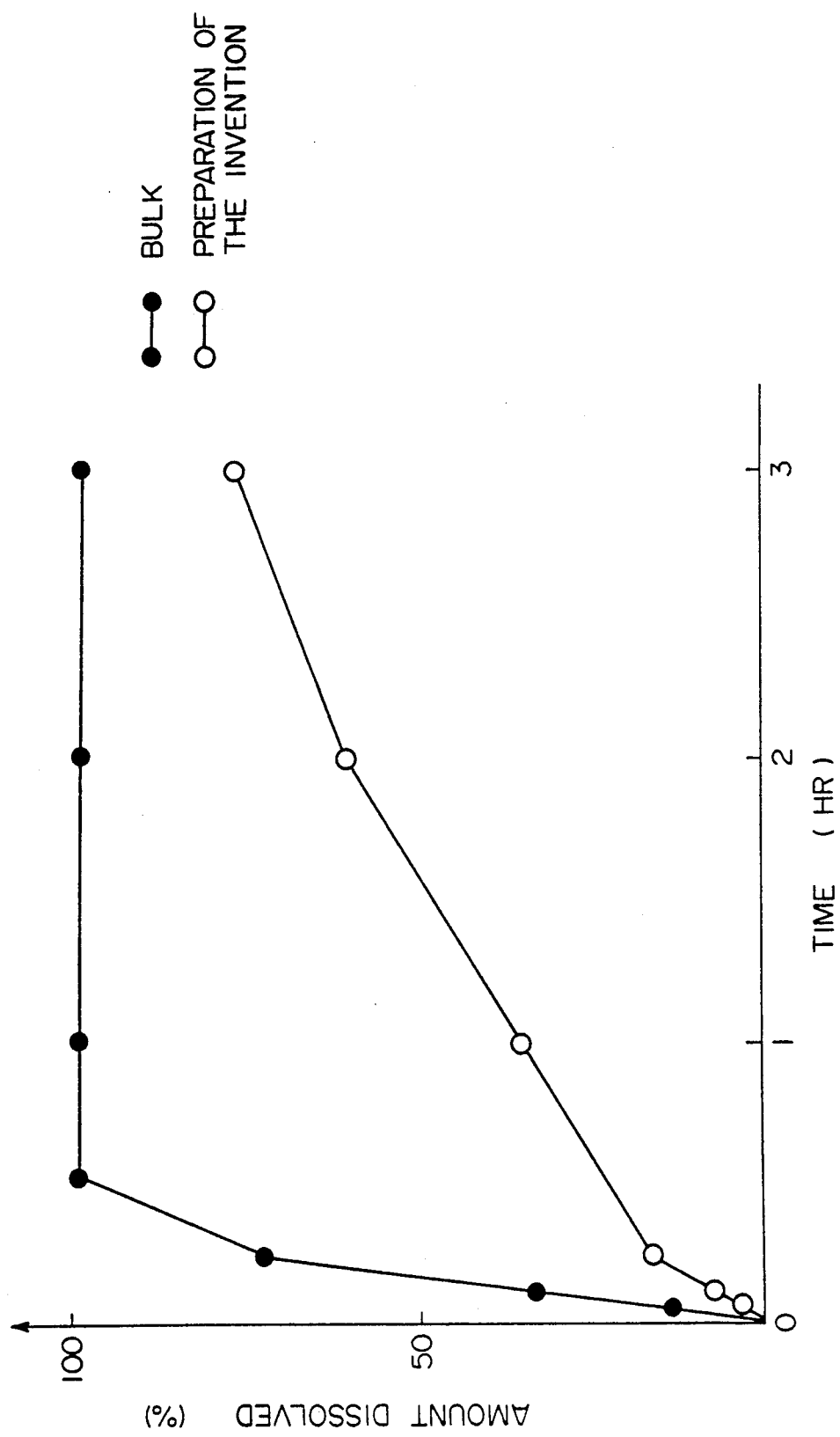

In the accompanying drawings:

FIG. 1 is a blood level-time characteristic diagram showing the bioavailability of the pharmaceutical preparation produced in Example 3 and theophylline bulk;

FIG. 2 is a dissolved amount-time characteristic diagram of the pharmaceutical preparation produced in Example 6 and theophylline bulk in a dissolution test conducted by the dissolution test method (second method) using a first liquid stipulated in the 11th Revised Edition of Japanese Pharmacopoeia; and FIG. 3 is a dissolved amount-time characteristic diagram of the pharmaceutical preparation produced in Example 6 and theophylline bulk in a dissolution test conducted by the dissolution test method (second method) using a second liquid stipulated in the 11th Revised Edition of Japanese Pharmacopoeia.

EXAMPLE 1

Three grams of polyvinylacetaldiethylaminoacetate ("AEA" for short) was dissolved in 150 g of deionized water with stirring. Furthermore, 47 g of 6-O-methylerythromycin A ("TE-031" for short) was put in the solution. The mixture was stirred by a vacuum stirring device (model PQ-3, made by Mizuho Kogyo Kabushiki Kaisha) to form a uniform suspension. The suspension was injected into a disc atomizer having a diameter of 70 mm and rotating at a speed of 3000 rpm at a flow rate of 70 ml/min. to form fine liquid droplets. Immediately then, the fine liquid droplets were introduced into a liquid nitrogen tank and frozen. They were classified in a classifier (model TM-50, made by Tokumasa Kosakusho) to collect fine frozen particles having a particle diameter of about 100 microns. The remaining frozen particles, which were rejected were recovered, and recycled to the suspension.

The resulting fine frozen particles having a uniform particle size were let fall at about 0° C. onto a powder bed of the air flow stirred type charged with an AEA powder pulverized to an average particle diameter of about 10 microns to allow the AEA powder to adhere to their surfaces. After the AEA powder had sufficiently adhered, the AEA coated particles were taken out and passed through a classifier to separate them from the non-adhering AEA powder. The coated particles were dried at 50° C. for 3 hours by a fluidized bed dryer to give a fine coated pharmaceutical preparation.

The preparation had a TE-031 content of 45.6%.

EXAMPLE 2

| AEA | 0.5% by weight |
| Hydroypropylmethyl-cellulose | 1.5% by weight |
| TE-031 | 23.0% by weight |
| Mixture of deionized water and methanol (4:1) | 75.0% by weight |

A uniform suspension of the above composition was prepared as in Example 1, and together with liquid nitrogen, sprayed from two fluid nozzles to give fine frozen particles. The frozen particles were treated as in Example 1. The resulting coated pharmaceutical preparation had a TE-031 content of 41.3%.

EXAMPLE 3

| Methylcellulose | 3.0% by weight |
| Theophylline | 27.0% by weight |
| Mixture of deionized water and methanol (1:19) | 70.0% by weight |

A uniform suspension having the above composition was sprayed under pressure into liquid nitrogen from a disc atomizer to freeze it. Then, as in Example 1, uniform fine frozen particles having an average particle diameter of 250 microns were obtained.

Then, the fine frozen particles were let fall onto a powder bed of hydroxypropylmethylcellulosephthalate maintained at 0° C. and having an average particle diameter of about 3 microns in an air flow-stirring type mixer to allow the powder to adhere to the surfaces of the particles. The coated particles were passed through a classifier to separate them from the powder bed, and dried at 50° C. for 3 hours by a fluidized bed dryer to give a fine coated pharmaceutical preparation.

The resulting preparation had a theophylline content of 32.3%.

EXAMPLE 4

| AEA | 1.5% by weight |
| Berberine chloride | 28.5% by weight |
| Deionized water | 70.0% by weight |

A uniform suspension of the above composition was used. Otherwise, as in Example 1, the suspension was frozen, and the frozen liquid droplets were let fall onto a powder bed of a mixture of AEA and carnauba wax (7:1, w/w) to give a fine coated pharmaceutical preparation having a berberine chloride content of 47.0%.

EXAMPLE 5

| AEA | 1.0% by weight |
|---|---|
| Hydroxypropylcellulose | 1.0% by weight |
| Ketoprofen | 28.0% by weight |
| Mixture of deionized water and ethanol (10:1) | 70.0% by weight |

In the same way as in Example 2, a uniform suspension having the above composition was frozen, and let fall onto a powder bed of a 3:1 (w/w) mixture of AEA and hydroxypropylcellulose to give a fine coated pharmaceutical preparation.

The resulting pharmaceutical preparation had a ketoprofen content of 47.3%.

EXAMPLE 6

| Hardened castor oil | 2.0% by weight |
|---|---|
| Hydroxypropylcellulose | 2.0% by weight |
| Talc | 1.0% by weight |
| Theophylline | 30.0% by weight |
| Mixture of deionized water and ethanol (1:19) | 65.0% by weight |

In the same way as in Example 2, a uniform suspension having the above composition was frozen, and let fall onto a powder bed of a 2:2:6 (w/w) mixture of hardened castor oil, hydroxypropylcellulose and carnauba wax to give a fine coated pharmaceutical preparation.

The resulting pharmaceutical preparation had a theophylline content of 52.1%.

TEST EXAMPLE 1

The pharmaceutical preparation formed in Example 1 was taken up in such an amount that it contained 500 mg of TE-031. It was then suspended in 25 ml of a 30% aqueous solution of sugar to prepare a syrup. Separately, 500 mg of TE-031 as a bulk was suspended likewise in 25 ml of a 30% aqueous solution of sugar, and used as a control. These types were administered in an amount of 1 ml of each to ten male volunteers and 10 female volunteers, and a bitterness test was conducted.

The results are shown in Table 1.

TABLE 1

| Subject | Sex | A | B | C | D | E |
|---|---|---|---|---|---|---|
| 1 | male | 0 | 0 | 1 | 2 | 7 |
|   | female | 0 | 0 | 2 | 4 | 4 |
| Control | male | 8 | 2 | 0 | 0 | 0 |
|   | female | 9 | 1 | 0 | 0 | 0 |

Standards of evaluation
A: considerably bitter
B: bitter
C: normal
D: not bitter
E: not bitter at all.

The results of this test show that the coated pharmaceutical preparation of Example 1 has a better masking of a bitter taste than the control.

TEST EXAMPLE 2

The angle of repose was measured on the coated pharmaceutical preparation produced in Example 3 and the theophylline bulk, and used as an index of flowability. The results are shown in Table 2.

TABLE 2

| Subject | 1st | 2nd | 3rd | Average |
|---|---|---|---|---|
| Example 3 | 33° | 31° | 33° | 32.3° |
| Bulk | 47° | 49° | 46° | 47.1° |

TEST EXAMPLE 3

The coated pharmaceutical preparation formed in Example 3 or the theophylline bulk was orally administered forcibly to Beagle dogs in an amount of 100 mg, as theophylline, per dog. The blood level of theophylline was measured by the crossover method on four dogs.

The results are shown in FIG. 1. The area under the curve (AUC) of the blood level-time characteristic curve, which is an index of bioavailability, in the coated pharmaceutical preparation of Example 3 was 99.8% of that in the theophylline bulk. The index of slow releasability, $T_{max}$, determined from the graph, was 1.0 hour for the bulk, and 3.5 hours for the pharmaceutical preparation of Example 3. The results show that the pharmaceutical preparation of Example 3 was rendered slow-releasing without substantially reducing the bioavailability of the theophylline bulk.

TEST EXAMPLE 4

The coated pharmaceutical preparation formed in Example 6 and the theophylline bulk were weighed in an amount of 100 mg as theophylline, and then subjected to a dissolution test under the following conditions by the dissolution test (second method) stipulated in the 11th Revised Edition of Japanese Pharmacopoeia.

Dissolution test conditions

Amount of the test liquid: 900 ml
Test liquid: the first or second liquid in accordance with the Japanese Pharmacopoeia.
Puddle rotating speed: 100 rpm
Temperature of the test liquid: 37°±0.5° C.

The results are shown in FIG. 2 (the first liquid was used) and FIG. 3 (the second liquid was used).

From the amount of dissolution-time, shown by the curves in FIGS. 2 and 3, it is seen that the coated pharmaceutical preparation of Example 6 was effectively rendered slow-releasing.

We claim:
1. A method of producing a coated pharmaceutical preparation, which comprises:
   cooling liquid droplets composed of a liquid medium and a drug dissolved or suspended in the liquid medium to a temperature of not higher than the freezing point of the liquid medium to form frozen particles containing the drug;
   classifying the frozen particles to isolate a desired particle size fraction having an average particle diameter of 5–500 microns;
   mixing the isolated fraction of frozen particles in a fluidized bed a powder of a coating material having a particle diameter not more than 1/5 the diameter of said particles at a temperature higher than the freezing point of the liquid medium to cause the powder of the coating material to adhere to the surfaces of said particles; and
   then removing the liquid medium from the coated particles.

2. The method of claim 1 in which the liquid medium is selected from the group consisting of water, methanol, ethanol, acetone and mixtures thereof.

3. The method of claim 1 wherein said liquid droplets additionally contain a binder.

4. The method of claim 3 in which the binder is selected from the group consisting of polyvinylacetaldiethylaminoacetate, polyvinylpyrrolidone, hydroxypropylcellulose, hydroxypropylmethylcellulose, carboxymethylcellulose sodium, ethylcellulose, starch and gelatin.

5. The method of claim 3 in which the total concentration of the drug and the binder in the liquid droplets is 5 to 70% by weight.

6. The method of claim 1 in which the liquid droplets are formed by spraying.

7. The method of claim 6 in which the liquid droplets are formed by using an atomizer.

8. The method of claim 1 in which the liquid droplets are cooled to a temperature at least 10° C. lower than the freezing point of the liquid medium.

9. The method of claim 1 in which the liquid droplets are cooled by contacting them with liquid nitrogen, liquefied carbon dioxide gas or liquid helium, or by use of an electrically cooled vessel.

10. The method of claim 1 in which the classifying is carried out by means of an air classifier or a sieving classifier.

11. The method of claim 1 in which the frozen particles isolated by classification have an average particle diameter of 5 to 500 microns.

12. The method of claim 1 in which the coating material is selected from the group consisting of polyvinylacetaldiethylaminoacetate, ethylcellulose, hydroxypropylcellulose, hydroxypropylmethylcellulose, hydroxypropylmethylcellulose phthalate, methyl cellulose, acrylic derivatives, stearyl alcohol, gelatin, carnauba wax, hardened castor oil, sucrose and talc.

13. The method of claim 1 in which the average particle diameter of the powder of the coating material is not more than 1/5 of that of the frozen particles isolated by classification.

14. The method of claim 1 in which the mixing of the fine frozen particles and the coating material is effected at a temperature at which the fine frozen particles do not substantially melt, and then gradually elevating the temperature.

* * * * *

UNITED STATES PATENT AND TRADEMARK OFFICE
CERTIFICATE OF CORRECTION

PATENT NO. : 5,017,383

DATED : May 21, 1991

INVENTOR(S) : Ozawa et al

It is certified that error appears in the above-identified patent and that said Letters Patent is hereby corrected as shown below:

Col. 7, line 46, "of each to" should read --to each of--.

Col. 8, line 61, after "bed" insert --of--.

Col. 10, line 4, delete --carried out--.

Signed and Sealed this

Twenty-second Day of December, 1992

Attest:

DOUGLAS B. COMER

Attesting Officer      Acting Commissioner of Patents and Trademarks